US010585024B1

(12) United States Patent
Bartko et al.

(10) Patent No.: US 10,585,024 B1
(45) Date of Patent: Mar. 10, 2020

(54) EXTRACTION OF MATERIALS FROM LIQUIDS (71) Applicant: BATTELLE MEMORIAL INSTITUTE, Columbus, OH (US)

(72) Inventors: Andrew P. Bartko, Worthington, OH (US); Kurt Blohm, Columbus, OH (US); Ryan W. Daly, Columbus, OH (US); Aaron M. Deal, Orient, OH (US); Scott M. Gibbons, Canal Winchester, OH (US); Susana Lira-Gonzalez, Columbus, OH (US); Benjamin J. Richetti, Columbus, OH (US); Nathan Roehr, Columbus, OH (US); Theodore J. Ronningen, Lewis Center, OH (US); Christopher Scheitlin, Columbus, OH (US)

(73) Assignee: BATTELLE MEMORIAL INSTITUTE, Columbus, OH (US)

(*) Notice: Subject to any disclaimer, the term of this patent is extended or adjusted under 35 U.S.C. 154(b) by 0 days.

(21) Appl. No.: 16/545,125

(22) Filed: Aug. 20, 2019

Related U.S. Application Data (60) Provisional application No. 62/720,211, filed on Aug. 21, 2018.

(51) Int. Cl.
*G01N 1/40* (2006.01)
*C02F 1/00* (2006.01)
(Continued)

(52) U.S. Cl.
CPC ........... *G01N 1/4077* (2013.01); *C02F 1/001* (2013.01); *C02F 1/008* (2013.01); *G01N 1/2813* (2013.01);
(Continued)

(58) Field of Classification Search
CPC .............. G01N 1/4077; G01N 1/2813; G01N 15/0606; C02F 1/001; C02F 1/008
(Continued)

(56) References Cited

U.S. PATENT DOCUMENTS

2003/0116487 A1  6/2003  Petersen
2003/0199100 A1  10/2003  Wick
(Continued)

FOREIGN PATENT DOCUMENTS

WO     2017/097604 A1    6/2017

OTHER PUBLICATIONS

Notification of Transmittal with the International Search Report and the Written Opinion of the International Searching Authority for PCT International Application No. PCT/US2019/047133; European Patent Office; Rijswijk, The Netherlands; dated Dec. 12, 2019.

*Primary Examiner* — Tarun Sinha
(74) *Attorney, Agent, or Firm* — Thomas E. Lees, LLC (57) ABSTRACT

An apparatus for extracting a material from a liquid includes a concentration stage having a tangential flow filter, a first path from the tangential flow filter, and a second path from the tangential flow filter. Under this configuration, the concentration stage accepts an initial liquid volume. A first liquid not having material collected by the tangential flow filter is passed along the first path, and concentrated liquid having material therein, which is entrapped by the filter, is directed to the second path. The apparatus also includes an aerosolizing stage coupled to the concentration stage that converts the concentrated liquid into an aerosol and a drying stage that dries the aerosol such that material extracted from the aerosol onto a material substrate.

20 Claims, 6 Drawing Sheets

(51) Int. Cl.
  *G01N 15/06*  (2006.01)
  *G01N 1/44*  (2006.01)
  *G01N 1/28*  (2006.01)
  *G01N 33/18*  (2006.01)

(52) U.S. Cl.
  CPC ........... *G01N 1/44* (2013.01); *G01N 15/0606* (2013.01); *C02F 2201/005* (2013.01); *C02F 2209/03* (2013.01); *C02F 2209/40* (2013.01); *G01N 33/18* (2013.01); *G01N 2001/4088* (2013.01); *G01N 2015/0687* (2013.01)

(58) Field of Classification Search
  USPC ........................................................ 73/61.72
  See application file for complete search history.

(56) References Cited

U.S. PATENT DOCUMENTS

| | | | |
|---|---|---|---|
| 2009/0126514 A1 | 5/2009 | Burroughs et al. | |
| 2009/0183554 A1 | 7/2009 | Grant et al. | |
| 2011/0059462 A1* | 3/2011 | Lim | G01N 1/4077 435/6.13 |
| 2011/0197685 A1* | 8/2011 | Alburty | G01N 1/4055 73/863.23 |
| 2012/0096925 A1* | 4/2012 | Hansen | G01N 1/2205 73/28.04 |
| 2017/0036935 A1* | 2/2017 | Peterson | C02F 9/00 |
| 2018/0224366 A1 | 8/2018 | Blackford et al. | |
| 2018/0347100 A1* | 12/2018 | Poy | D06F 39/10 |

* cited by examiner

```
                  100
                    ↘
    ┌─────────────────────────────────────────────┐
    │                                             │
102 │    104              108            110      │
    │  CONCENTRATION                              │
 LIQUID →    AND      →  ANALYZER    →   OUTPUT  │
 SOURCE  │ AEROSOLIZING │                         │
    │   APPARATUS     │                           │
    │       ↓     ↑      ↑                        │
    │     DRAIN  CONTROLLER                       │
    │      106      112                           │
    └─────────────────────────────────────────────┘
```

502
        ┌─────────────────────────────────────┐
        │   INTRODUCE AN INITIAL LIQUID VOLUME │ ──┐ INPUT STAGE
        └─────────────────────────────────────┘
516                        ↓
  ┌ ─ ─ ─ ┐  504
  │CLEANING│   ┌─────────────────────────────────────┐
  │ CYCLE  │──▶│ DIRECT THE INITIAL LIQUID VOLUME     │ ──┐
  └ ─ ─ ─ ┘   │ THROUGH A TANGENTIAL FLOW FILTER     │   │ CONCENTRATION
              └─────────────────────────────────────┘   │ STAGE
         506                ↓                           │
              ┌─────────────────────────────────────┐   │
              │ DIRECT A CONCENTRATE LIQUID INTO A   │ ──┘
              │ STORAGE CONTAINER                    │
              └─────────────────────────────────────┘
                            ↓
         508  ┌─────────────────────────────────────┐
              │ INTRODUCE A PORTION OF THE CONCENTRATE│──┐
              │ LIQUID INTO A NEBULIZER              │  │ AEROSOLIZATION
              └─────────────────────────────────────┘  │ STAGE
         510                ↓                          │
              ┌─────────────────────────────────────┐  │
              │ PRODUCE AEROSOLIZED LIQUID DROPLETS  │──┘
              └─────────────────────────────────────┘
                            ↓
         512  ┌─────────────────────────────────────┐
              │ HEAT THE AEROSOLIZED LIQUID DROPLETS │── DRYING STAGE
              │ IN A DRYING CHAMBER                  │
              └─────────────────────────────────────┘
                            ↓
         514  ┌─────────────────────────────────────┐
              │ PROVIDE AN AEROSOLIZED MATERIAL TO A │── MATERIAL
              │ PROCESSING STATION                   │   COLLECTION/TESTING
              └─────────────────────────────────────┘
```

602 CONCENTRATION STAGE

604 TANGENTIAL FLOW FILTER 608  606  612

610  614

DRAIN

620 CONTROLLER

616 AEROSOLIZING STAGE

618 DRYING STAGE

622 ANALYZER

FIG. 6 ized liquid droplets and heating the aerosolized liquid droplets in a drying chamber to extract the material from the liquid droplets.

EXTRACTION OF MATERIALS FROM LIQUIDS

CROSS REFERENCE TO RELATED APPLICATIONS

This application claims the benefit of U.S. Provisional Patent Application Ser. No. 62/720,211, filed Aug. 21, 2018, having the title EXTRACTION OF MATERIAL FROM A LIQUID, the disclosure of which is hereby incorporated by reference.

BACKGROUND

The present disclosure relates generally to the extraction of a material from a liquid, and more particularly to the concentration, aerosolization, collection, detection, analysis, or combinations thereof, of a liquid sample comprising the material.

A variety of liquids, including water, destined for consumption or injection must be monitored and controlled for the presence of harmful contaminants, such as bacteria, fungi, and mold. Furthermore, liquids used, for example, in laboratory testing, manufacturing, and other types of facilities may also need to be monitored to detect the presence of such contaminants.

BRIEF SUMMARY

In accordance with an aspect of the present disclosure, an apparatus for extracting a material from a liquid comprises a concentration stage, an aerosolizing stage, and a drying stage. The concentration stage accepts an initial liquid volume, where the initial liquid volume has an initial concentration of a material. Moreover, the concentration stage comprises a tangential flow filter, a first path from the tangential flow filter, and a second path from the tangential flow filter. The tangential flow filter accepts the initial liquid volume and collects the material from the initial liquid volume. More particularly, the tangential flow filter produces a permeate that is substantially devoid of the collected material, and the tangential flow filter produces a retentate that has a higher concentration of the material than the initial concentration. In this regard, the first path from the tangential flow filter defines a conduit for the permeate, and the second path from the tangential flow filter defines a conduit for the retentate. The aerosolizing stage is coupled to the second path and converts the retentate into an aerosol. The drying stage dries the aerosol to extract the material and collects the extracted material onto a material substrate.

In example embodiments, the permeate represents a first portion of the liquid volume introduced to the concentration stage. The permeate, which does not have material collected by the tangential flow filter, is passed along the first path. Correspondingly, the retentate represents a second portion of the liquid volume introduced to the concentration stage. The retentate defines a concentrated liquid having material therein, which is entrapped by the tangential flow filter, and is directed to the second path.

In accordance with another aspect of the present disclosure, a process for extracting materials from liquids is provided. The process comprises introducing an initial liquid volume into a concentration stage, the initial liquid volume having an initial concentration of a material. The process also comprises directing the initial liquid volume into a tangential flow filter for entrapping the material to produce a concentrated liquid having a higher concentration of the material than the initial concentration. The process further comprises directing the concentrated liquid out of the concentration stage. The process still further comprises introducing a portion of the concentrated liquid into a nebulizer to produce aerosolized liquid droplets and heating the aerosolized liquid droplets in a drying chamber to extract the material from the liquid droplets.

According to yet further aspects of the present disclosure, an apparatus for extracting materials from liquids, comprises a concentration stage, an aerosolizing stage, a drying stage, a controller, and an analyzer. The concentration stage accepts an initial liquid volume having an initial concentration of a material. Moreover, the concentration stage comprises a tangential flow filter, a permeate path, and a retentate path. The tangential flow filter accepts the initial liquid volume, collects the material from the initial liquid volume, produces a permeate that is substantially devoid of the collected material, and produces a retentate having a higher concentration of the material than the initial concentration. The permeate path comprises a conduit having a flow meter, and a permeate control valve there-along. Moreover, the permeate path directs the permeate from the tangential flow filter. The retentate path comprises a conduit having a retentate control valve there-along. The retentate path directs the retentate from the tangential flow filter. The aerosolizing stage is coupled to the retentate path and converts the retentate into an aerosol. The drying stage dries the aerosol to extract the material, wherein the extracted material is collected onto a material substrate. The controller is coupled to the concentration stage, and to the aerosolizing stage, wherein the controller automates liquid sample collection. The analyzer is coupled to the controller, which operates in parallel with the liquid sample collection to analyze the material collected onto the material substrate.

BRIEF DESCRIPTION OF THE DRAWINGS

The following detailed description of various aspects of the present disclosure may be best understood when read in conjunction with the following drawings, where like structure is indicated with like reference numerals, and in which.

DETAILED DESCRIPTION

Liquids (including, but not limited to water) may be utilized for tasks that can include consumption, injection, food preparation, industrial processes, pharmaceutical processes, etc. However, such liquids may carry harmful microorganisms such as bacteria, fungi and mold. Depending on the use of the liquid, an acceptable concentration level may be established. For instance, in an example implementation, an acceptable concentration of microorganisms may be less than 1 cell per milliliter (mL). In addition, the species and/or strains of microorganisms in the liquid may need to be determined. For instance, depending upon the use of the liquid, different species of microorganism can have significantly different impacts, including different health impacts. Accordingly, aspects herein concentrate and collect liquids. The concentrated and collected liquid can then be monitored for the presence of harmful microorganisms.

Responsive to the detection of harmful microorganisms, workflows can thus be controlled, such as to stop industrial processes, trigger alarms, issue reports, flag detection, identify detected species, identify detected strains, identify detected concentrations, perform classification and report results, etc., as described more fully herein.

Moreover, aspects herein address issues with monitoring liquids with low liquid concentrations by processing a sufficient volume of liquid, such as to ensure the statistical accuracy of detection or quantification, minimize the loss of particulates (e.g., cellular material), leave the cellular material in a format compatible with follow-on analysis, etc.

Aspects of the present disclosure are directed to methods, apparatus, and systems for automatically concentrating, aerosolizing, drying, collecting, monitoring, combinations thereof, etc., particulates (e.g., cellular material) that are suspended in a liquid source. More particularly, such approaches accept an initial liquid volume and apply filtration to generate a concentrate (a reduced liquid volume that contains the cellular material at a higher concentration). Aspects herein also aerosolize that concentrate (e.g., through a nebulizer) and dry the aerosol to separate the material (e.g., cells) from the liquid. Moreover, in certain embodiments, the concentrate is monitored, e.g., by transferring the concentrate to an analyzer, or by monitoring the concentrate in the same apparatus that dries the aerosol. Notably, the approaches herein yield a decrease in time to result, a decrease in labor investment, or a combination thereof.

Yet further, certain aspects of the present disclosure provide for a control scheme, which may be executed by a computer or other processor running executable computer code. In this regard, the computer code is read out and is executed by the system to automate the processes described more fully herein, e.g., to automatically concentrate, aerosolize, dry, collect, monitor, analyze, control, combinations thereof, etc., cellular material that is suspended in a liquid source.

According to further aspects of the present disclosure, an apparatus and process are provided to extract materials from liquids. A liquid of interest, at a first, lower concentration of material, is reduced to a concentrated liquid comprising a smaller liquid volume containing material at a higher concentration. The concentrated liquid is then aerosolized and at least partially dried to separate the material from the liquid. The liquid may comprise, for example, water. In other examples, the liquid may include, but is not limited to, a small molecule formulation. A small molecule formulation includes, for example, an aqueous sample that includes other components such as salts, surfactants, antiseptic molecules, etc. Other aqueous and non-aqueous liquids can include methanol, ethanol, wine, beer, liquor, organic solvents, milk, etc.

The material to be extracted from the liquid may comprise, for example, particulates such as one or more microorganisms, including bacteria, protozoa, fungi, algae, viruses, and fragments or portions thereof. The material may also comprise nucleic acids, proteins, polymers, and other biological and non-biological particles and contaminants. The material may be collected and subjected to additional analysis to detect and identify the presence of microorganisms and/or other types of particles.

Figure 1:
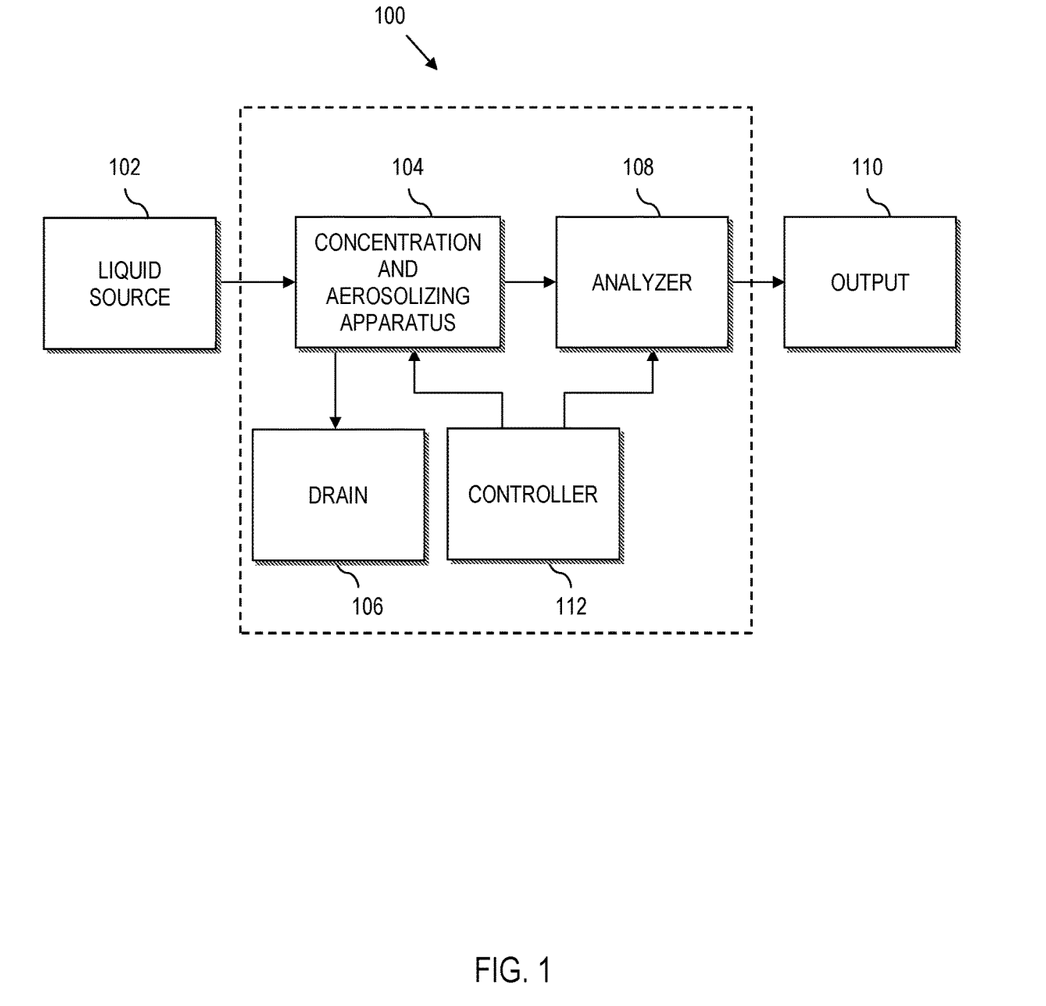
FIG. 1 illustrates a block diagram of a system for extracting and analyzing a material from a liquid sample, in accordance with various aspects of the present disclosure.

Referring now to the drawings and in particular to FIG. 1, a block diagram illustrates a system 100 for collecting, concentrating, and monitoring for materials suspended in a liquid, according to various aspects of the present disclosure. In practical applications, liquid is provided from a liquid source 102. As will be described in greater detail herein, the liquid source 102 can comprise water collected from a water supply, a liquid sample (water or otherwise) collected from an impactor, a liquid (water or otherwise) extracted from a manufacturing or pharmaceutical process, etc.

A concentration and aerosolizing apparatus 104 receives liquid from the liquid source 102. In this regard, the concentration and aerosolizing apparatus 104 extracts materials from liquids, e.g., to prepare a sample for monitoring or other analysis. This may comprise collecting, concentrating, aerosolizing, drying, incubating, combinations thereof, or other processing steps necessary to prepare a sample for subsequent analysis. For instance, in an example implementation, the concentration and aerosolizing apparatus 104 accepts an initial liquid volume from the liquid source 102, and filters material from the initial liquid volume, producing a permeate that is substantially devoid of the collected material, and producing a retentate that has a higher concentration of the material than the initial concentration. The retentate is directed to an aerosolizing stage that converts the retentate into an aerosol, and a drying stage dries the aerosol to extract the material, e.g., onto a material substrate. Example implementations of concentration, aerosolizing, drying, combinations thereof, etc., are described in greater detail herein, e.g., with regard to FIGS. 2-6.

An optional drain 106 can be provided in certain embodiments, and is used to redirect liquid, e.g., water, a carrier, residual, waste, or other fluid not necessary for subsequent analysis, to a suitable destination, e.g., for disposal, recycling, or other use.

An analyzer 108 accepts the material (or a sample thereof), collected by the concentration and aerosolizing apparatus 104 to perform a desired analysis. Here, the analyzer 108 can utilize fluorescence, Raman Spectroscopy, imaging, a microscope, chemistry, other techniques, combinations thereof, etc. to monitor the collected material, analyze the material to provide an indication of the contents of the sample, combinations thereof, etc.

An output 110 provides a result from the analyzer 108. Here, the output 110 can be an alarm, a message, a report, combinations thereof, etc. Moreover, the output 110 can be expressed in different manifestations. For instance, the output 110 can be based upon a detected broad classification—e.g., the sample includes biological material. The output 110 can be based upon a computed statistical probability that exceeds a threshold. For instance, there is a 90% likelihood that the sample includes a biological material. In other examples, the output 110 can be based upon a detection exceeding a predetermined criterion or set of criteria, e.g., material exceeds a concentration of x part(s) per volume, e.g., 1 part per milliliter (mL); biological material exceeds 1 cell per milliliter (mL) regardless of total material content), etc. Moreover, the output 110 can include precise species/strain identification or classification, including the detection of multiple species. The output 100 can also comprise an email, a text message, other alert, a workflow, e.g., to start or stop a process, a command to start, stop, continue, etc., an industrial machine/process based upon the monitoring results, a command to start, stop, continue, etc., a pharmaceutical machine/process based upon the monitoring results etc. Yet further, any combination of the above can be implemented.

A controller 112 couples to the concentration and aerosolizing system 104 and the analyzer 108, as shown. The controller 112 provides the control, timing, and synchronization required for the monitoring/analysis of liquid samples. For instance, the controller 112 can control the concentration and aerosolizing system 104 to collect a liquid sample and pass the sample to the analyzer 108 for subsequent analysis. The controller 112 can also interface with external electronics, e.g., to carry out processes defined by the output 110, e.g., to control downstream machines/processes, send alerts, etc.

Figure 2:
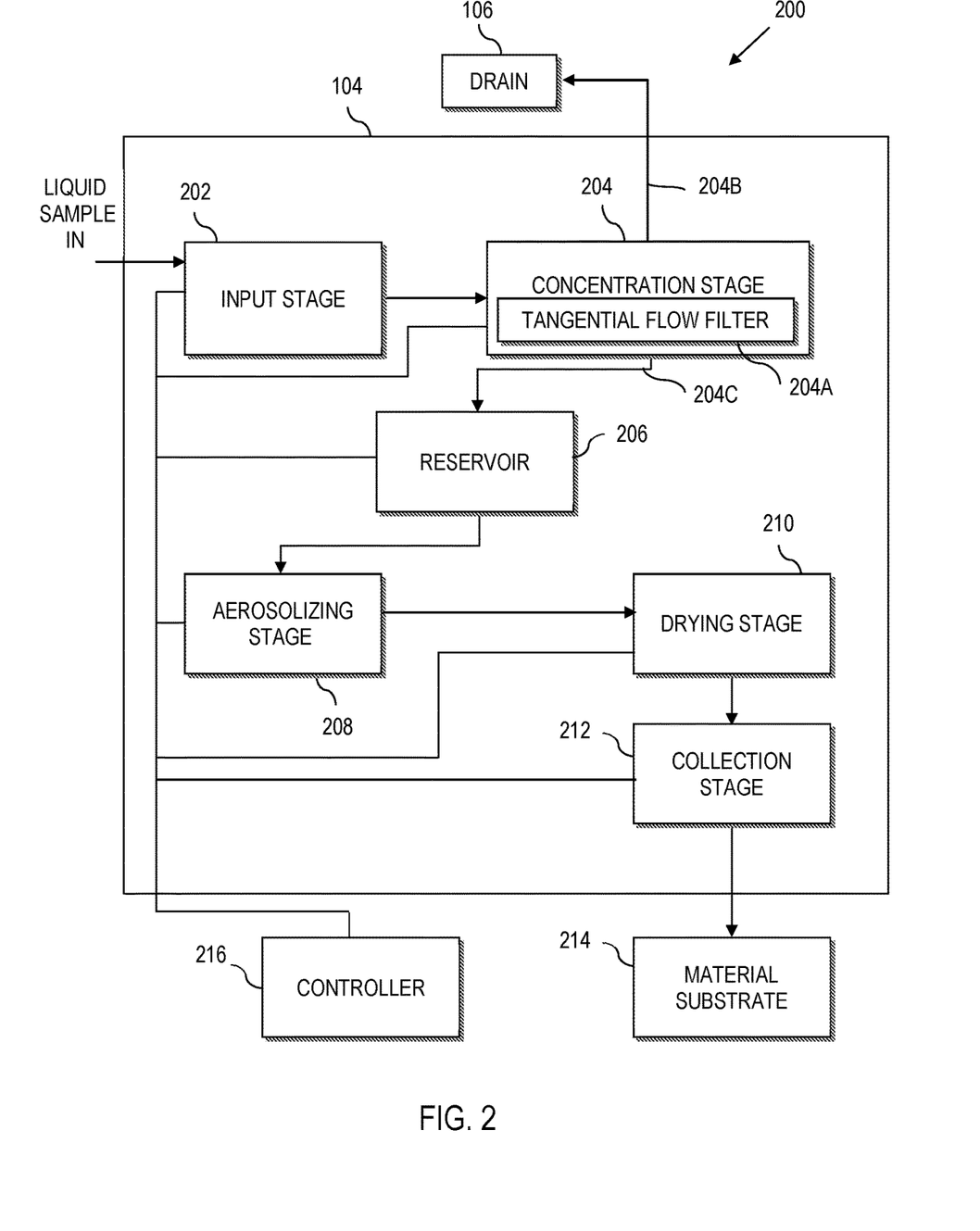
FIG. 2 illustrates a block diagram of an apparatus that extracts materials from liquids, in accordance with various aspects of the present disclosure.

Referring to FIG. 2, a block diagram 200 illustrates an apparatus for extracting a material from a liquid sample, in accordance with various aspects of the present disclosure. The block diagram 200 further illustrates example components capable of implementing the concentration and aerosolizing apparatus 104 of FIG. 1.

As will be described in greater detail herein, an apparatus for extracting a material from a liquid (e.g., concentration and aerosolizing apparatus) comprises in general, a concentration stage, an aerosolizing stage, and a drying stage. The apparatus can also include additional components that each may support one or more of functions, such as concentration, storing, aerosolizing, and drying, etc.

As illustrated, an example concentration and aerosolizing apparatus 104 includes an optional input stage 202 that serves as an input for obtaining a liquid sample.

A concentration stage 204 is coupled to the input stage 202 and is operatively configured to receive the obtained liquid sample from the input stage 202. The concentration stage 204 converts a relatively large volume of liquid having a low concentration of interest, to a relatively lower volume of liquid with a relatively higher concentration of interest.

In general, the concentration stage 204 can comprise one or more control valves that define paths through the apparatus. The control valves are controlled (e.g., by the controller 112 of FIG. 1) to control a flow of the liquid through the concentration and aerosolizing apparatus 104. The concentration stage 204 may also comprise a pressure transmitter or regulator that controls a pressure of the liquid as it is introduced into the system. Here, the pressure regulator may be located upstream of a first control valve. As used herein, the term "upstream" refers to a point located toward a sample introduction port or otherwise opposite a flow direction, and the term "downstream" refers to a point located toward an exit, such as a drain line, or otherwise with a flow direction.

As will be described in greater detail herein, in an example embodiment, the concentration stage 204 comprises a tangential flow filter 204A, a first path 204B from the tangential flow filter 204A, and a second path 204C from the tangential flow filter 204A. More particularly, the tangential flow filter 204A accepts an initial liquid volume (e.g., from the input stage 202). The tangential flow filter 204 further collects material from the initial liquid volume, produces a permeate that is substantially devoid of the collected material, and produces a retentate that has a higher concentration of the material than the initial concentration.

A first portion of the liquid volume that is introduced to the concentration stage 204, which does not have material collected by the tangential flow filter (the permeate), is directed along the first path 204B, e.g., to drain 106. Correspondingly, a second portion of the liquid volume introduced to the concentration stage 204, defining a concentrated liquid having material therein, which is entrapped by the tangential flow filter (the retentate), is directed along the second path 204C.

An optional reservoir 206 can receive the output of the concentration stage 204, e.g., to collect the retentate directed along the second path 204C. The reservoir 206 serves as a holding area until a suitable time for subsequent analysis. For instance, the reservoir 206 may accumulate liquid until such time as a suitable concentration is built up, until such time as a predetermined cycle has run, until such time as a predetermined amount of liquid has built up, until a downstream component requests liquid, until a trigger occurs requiring a sample analysis, or based upon any other factor(s), e.g., that can be automated, e.g., based upon computer control.

An aerosolizing stage 208 coupled to the second path 204C receives liquid (e.g., optionally from the reservoir 206 where provided) and converts the retentate into an aerosol, e.g., using a nebulizer or other suitable hardware.

A drying stage 210 dries the aerosolize (representing an aerosolized sample), which extracts the material from any remaining liquid content. In an example embodiment, the drying stage 210 dries the aerosol such that material extracted from the aerosol is collected onto a material substrate.

An optional collection stage 212 receives the dried sample and can thus provide a concentrated and prepared sample for subsequent analysis. In this regard, the sample can be provided on a suitable material substrate 214. The sample substrate 214 is a substrate that is compatible with the associated analysis technology, storage requirements, collection requirements, combinations thereof, etc.

An optional controller 216 (e.g., in addition to, or in lieu of the controller 112, FIG. 1) can be provided to automate or semi-automate material concentration, aerosolizing, drying, collecting, combinations thereof, etc. As illustrated, the controller 216 is communicably coupled to one or more stages of the concentration and aerosolizing apparatus 104, e.g., the input stage 202, concentration stage 204, reservoir 206, aerosolizing stage 208, drying stage 210, collection stage 212, etc. Here, the controller 216 can communicate with controllable valves, meters, sensors, or other fixtures in order to implement component control, timing, etc., examples of which are described more fully herein.

Figure 3:
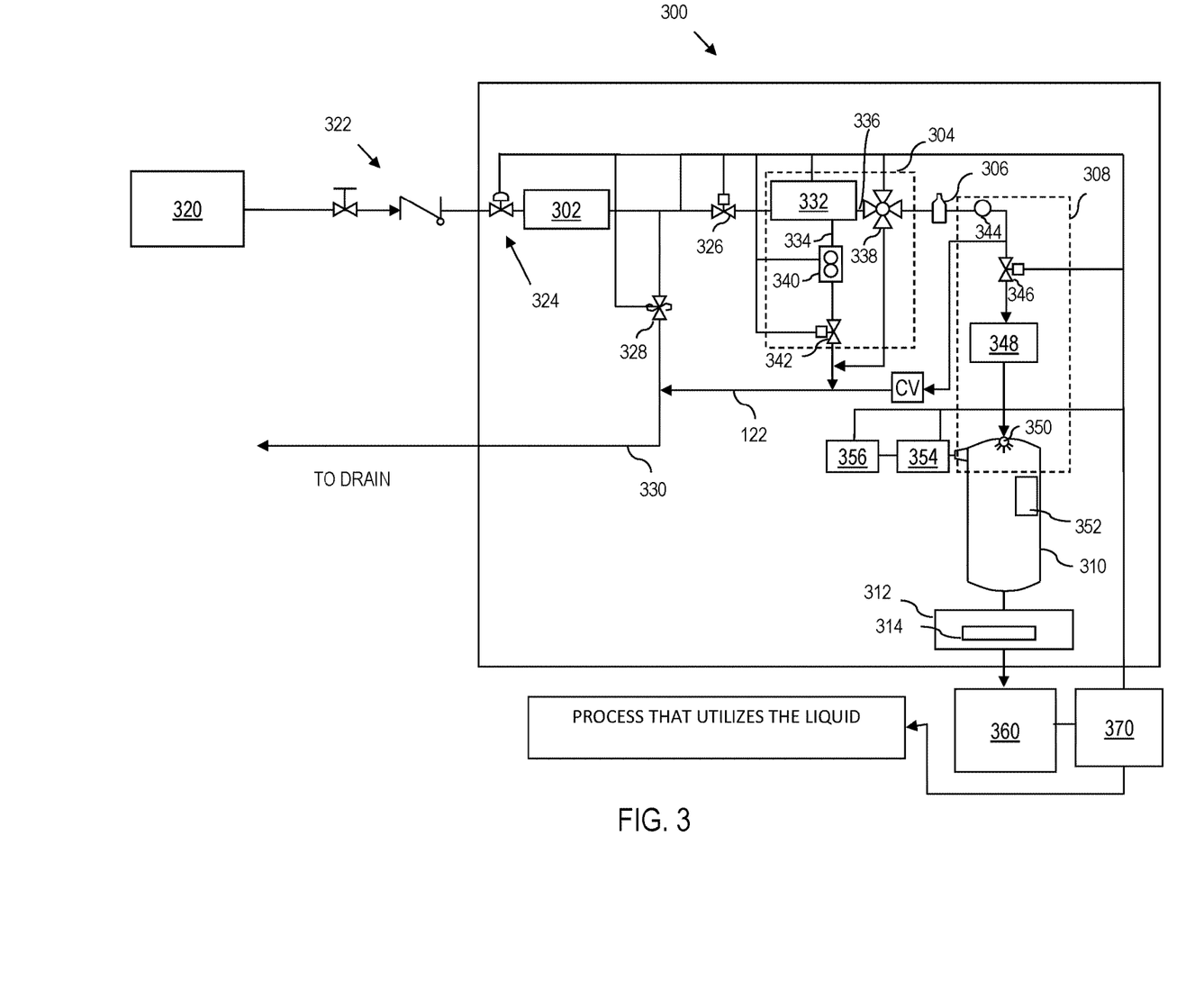
FIG. 3 is a schematic diagram of a system for extracting a material from a liquid sample, in accordance with various aspects of the present disclosure.

Referring to FIG. 3, a schematic diagram of an apparatus 300 for extracting a material from a liquid sample is illustrated, in accordance with various aspects of the present disclosure. In this regard, the system 300 is an example of concentration and aerosolizing apparatus 104 of FIG. 1 and/or FIG. 2. As such, like elements between FIG. 2 and FIG. 3 are illustrated with corresponding reference numerals 100 higher in FIG. 3 than the counterpart in FIG. 2.

The apparatus 300 accepts a volume of liquid and extracts a sample therefrom. In this regard, the system 300 is also referred to herein as a liquid sample adapter (LSA).

As an overview, in a manner analogous to FIG. 2, the LSA comprises an input stage 302 that provides a liquid to a concentration stage 304. The output of the concentration stage 304 is stored in a reservoir 306. An aerosolizing stage 308 pulls liquid from the reservoir 306 and aerosolizes the liquid to define a sample. The sample is dried by a drying stage 310 and is accumulated at a collection stage 312 on a material substrate 314 for subsequent analysis.

In more specific detail, a liquid source 320 (e.g. analogous to the liquid source 102 of FIG. 1) provides a source of liquid for evaluation. In an example embodiment, the liquid source 320 can comprise a client water system, supply of liquid in a manufacturing, industrial, or pharmaceutical application, supply from a sample collector, etc. In this regard, the liquid source 320 can provide the liquid to the system 300 via various valves, pipes, tubing, conduit, or other appropriate conveyance components (collectively supply fixtures 322).

The input stage 302 accepts an initial volume of liquid from the liquid source 320. In this regard, the system 300 can include input fixtures 324 (e.g., piping, valves, fittings, pumps, check valves, etc.) to couple the liquid from the liquid source 320 to the system 300. In an example implementation, the input stage 302, e.g., via a liquid introduction port and an input control valve, accepts a volume of liquid, on the order of 1 to 100 liters, for processing. In an example implementation, this "initial volume" is introduced at an elevated pressure that is regulated by the LSA to be in the range of 15 to 25 pounds per square inch (PSI). This controlled but elevated pressure provides the motive force for the concentration stage 304. The LSA regulates the pressure so that the liquid source 320 can have variable characteristics, including a wide range of pressures, the liquid source 320 can be static or flowing, etc.

A first control valve 326 controls the flow of liquid from the input stage 302 to the concentration stage 304. An optional second control valve 328 can be opened to divert liquid to a suitable drain, e.g., via a suitable drainage line 330.

In the concentration stage 304, the initial volume is directed via the first control valve 326 into a tangential flow filter 332. A flow rate into the tangential flow filter 332 is controlled by the regulated pressure of the system 300. The tangential flow filter 332 is selected so that liquid passes through a first path, designated a permeate path 334, as the "permeate", but cellular material is retained inside the tangential flow filter 332, in the "retentate" volume, which will subsequently be expelled from the tangential flow filter 332 via a second path, designated a retentate path 336, as described more fully herein.

In an example embodiment, the permeate path 334 includes a flow meter 340 and a permeate control valve 342. Correspondingly, the retentate path 336 includes a retentate control valve 338. In this manner, the permeate control valve 342 is open and the retentate control valve 338 is closed during collection. In another example, the retentate control valve 338 comprises a closed position, an open position, and an open to drain position, which provides for a drain path to prime and clean the tangential flow filter 332 by directing fluid to a drain line, bypassing the aerosolizing stage 308. For instance, the drain path can direct the liquid through the concentration stage and into the drain line without entering the aerosolizing stage 308.

As illustrated, as the initial volume is passing through the tangential flow filter 332, a retentate control valve 338 blocks the retentate outflow, leading to an accumulation of cellular material inside the tangential flow filter 332 in a "concentrated liquid". The concentrated liquid has a higher cell density (cells per unit volume) than the initial volume.

The remaining liquid, e.g., the non-concentrated liquid, is directed out the permeate path 334 and passes through a flow meter 340 to meter the amount of liquid input into the system. Here, a permeate control valve 342 is open so that the non-concentrated liquid can be disposed, e.g., via the drainage line 330.

Once the initial volume has passed across the tangential flow filter 332, as verified by the liquid flow meter 340, the permeate path 334 is closed by the permeate control valve 342. The control valve 326 can also be closed to verify that only the metered initial input volume of liquid is being processed. In this regard, the permeate control valve 342 is open while the initial volume of liquid is being processed by the tangential flow filter 332 so that liquid stripped of material can be removed from the system 300, e.g., via the drainage line 330.

Moreover, after a suitable sample (concentrate) has been collected, the permeate path 334 is closed (e.g., via the permeate control valve 342) and the retentate path 336 is opened. The concentrated liquid, with the cellular material entrained, is flushed out of the tangential flow filter 332 and into the liquid reservoir 306. The flow rate of this flush is controlled by the regulated pressure. The volume of concentrated liquid flushed from the tangential flow filter 332 is controlled by the time the retentate control valve 338 is open.

In certain embodiments, the apparatus can comprise a concentrated liquid reservoir located downstream of the tangential flow filter, and a pressure regulator that controls a pressure of the liquid in the concentration stage, the liquid in the concentration stage operated at a higher pressure than a pressure of a liquid source.

For instance, in the illustrated embodiment, the reservoir 306 receives and holds the retentate until the aerosolizing stage 308 initiates an aerosolizing operation. As soon as the flush has completed and the retentate control valve 338 has closed, another concentration stage 304 can be initiated, running in parallel with the aerosolizing stage 308. This parallel processing reduces the effective time per sample and allows for the liquid source to be processed close to continuously.

In example embodiments, the aerosolizing stage 308 comprises a peristaltic pump and a nebulizer, and the drying stage 310 comprises a drying chamber. Here, the peristaltic pump may control a flow of the liquid into the nebulizer, which can be at a flow rate substantially equal to a drying capacity of the drying chamber. The nebulizer receives the liquid and coverts the received liquid into aerosolized liquid droplets, and the drying chamber receives the aerosolized liquid droplets and separates cellular material from the droplets. In some embodiments, the peristaltic pump controls the flow of the liquid into the nebulizer at a flow rate, the flow rate substantially proportional to a drying capacity of the drying chamber.

In the aerosolizing stage 308, a pump 344 draws the concentrated liquid out of the reservoir 306. The drawn liquid is passed via an aerosolizing control valve 346 through a conduit where the liquid is measured by a bubble/air liquid sensor 348, and is injected into a nebulizer 350, e.g., via a micro bore tubing. The nebulizer 350 converts the liquid stream into aerosolized liquid droplets. The droplets pass through a drying chamber 352 of the drying stage 310, and the liquid evaporates, leaving the cells in the airstream. Any cellular material in the concentrated liquid is thereby separated from the liquid and aerosolized. The aerosolized, separated, and dry cellular material is available for analysis or collection.

The aerosolizing pump 344 is selected to control the liquid flow at a flow rate that matches the drying capacity of the aerosol drying chamber of the drying stage 310. By way of example, a rate in the range of 0.01 to 0.1 milliliter per minute may be implemented in a practical implementation.

The temperature of the drying chamber 352 of the drying stage 310 is controlled by a temperature control loop 354, and heaters are attached to the dryer to elevate its temperature. Makeup air entering the dryer can be heated or dried, as necessary, depending on the environmental temperature and humidity. Makeup air entering the dryer is filtered by a filter 356 to ensure that no cellular particles are introduced as contaminants in the air stream.

After drying, the material is collected at the collection stage 312, e.g., onto the material substrate 314, for transport to an analyzer 360, e.g., analogous to the analyzer 108 described more fully with regard to FIG. 1.

The system 300 includes a controller 370, e.g., a control board running software needed to automate one or more of the operations described herein. In some embodiments, the controller 370 also interfaces with another system, such as the analyzer 360, in order to operate synchronously with the analyzer 360. Synchronization allows for analysis to also run in parallel with sample preparation, further reducing time to result. Here, the controller 370 is analogous to the controller 216 (FIG. 2) and/or controller 112 (FIG. 1).

More particularly, to facilitate automation, the controller 370 is controllably coupled to the various valves, meters, sensors, etc. For instance, in the illustrated example, the controller 370 is coupled to the input control valve 324 to enable fluid to flow into the input stage. In certain embodiments, controller 370 controls the input control valve 324 and other necessary hardware, e.g., pump, pressure regulator, etc., as the application dictates, to input the liquid as a predefined pressure, which can be set, regulated, etc. via control of the controller 370.

To concentrate material, the controller 370 opens the first control valve 326, and closes the second control valve 328. This causes fluid to flow into the tangential flow filter 322. The controller 370 can close the first control valve 326 and open the second control valve 328 to drain any excessive collected fluid, once an acceptable collection operation is performed.

In an example implementation, the controller 370 controls the retentate control valve 338 to select one of a closed position, an "open to reservoir" position, and an "open to drain" position. As described herein, the controller 370 controls the retentate control valve 338 to the "open to drain" position for operations requiring that the LSA is automatically primed and cleaned. Using this "open to drain" position, the controller 370 directs liquid through the filter and out to drain 330 without passing through the aerosolizing components.

During material collection, the controller 370 controls the retentate control valve 338 to be in a closed position. The controller 370 also controls the permeate control valve 342 to be open. As material is collected by the tangential flow filter 322, the controller 370 monitors the waste liquid via the liquid flow meter 340. The liquid flow meter 340 used during the concentration stage quantifies the initial volume. This information is stored by the control software and is available for subsequent analyses where the material found may need to be quantified relative to the initial volume, e.g., by calculating a cellular concentration.

Once the controller 370 detects a target, e.g., a predetermined amount of metered liquid via the liquid flow meter 340, after a predetermined time period, after a predetermined amount of material is built up in the tangential flow meter, other triggers, combinations thereof, etc., the controller 370 closes the permeate control valve 342 and opens the retentate control valve 338 to the second position "open to reservoir". This allows the low volume, high concentration liquid to flow from the tangential flow filter 322 to the reservoir 306.

The controller 370 closes the retentate control valve 338 once the liquid transfers from the tangential flow filter 322 to the reservoir 306. The controller 370 then controls the pump 344 and opens the aerosolizing control valve 346 to draw the concentrated liquid into the aerosolizing stage 308. The controller 370 reads the bubble/air liquid sensor 348 to determine when the fluid is extracted from the reservoir 306.

The controller 370 controls the nebulizer 350 to convert the liquid with material entrapped therein, to an aerosol, which allows the liquid to be evaporated by the dryer, and the material to be collected onto the material substrate 314. Here, the controller 370 controls the temperature of the drying stage 310, e.g., via temperature control loop 354 and the flow rate from the pump 344, so that the droplets that pass through the drying chamber 352 of the drying stage 310, evaporate leaving the cells in the airstream, thereby separating the material on to the material substrate.

In some embodiments, the controller 370 may also be coupled to downstream electronics, e.g., to an industrial or pharmaceutical manufacturing process that utilizes the liquid. This can be useful to automate machine start/stop conditions based upon suitability of the liquid.

All components in the LSA are selected to be capable of sterilization and resistant to microbial contamination. This reduces the risk that the aerosolized sample is contaminated by microbial material contained inside the LSA. For analysis applications, contamination would lead to false positives and inaccurate quantification of cellular material.

Moreover, while the above-example implementations have focused on extracting cellular material from the initial volume, other particulates can be extracted with the LSA. For instance, the tangential flow filter can be selected to determine what size range of particles are retained and which are excluded. Also, other non-soluble particles, including proteins and polymers, can extracted.

Figure 4:
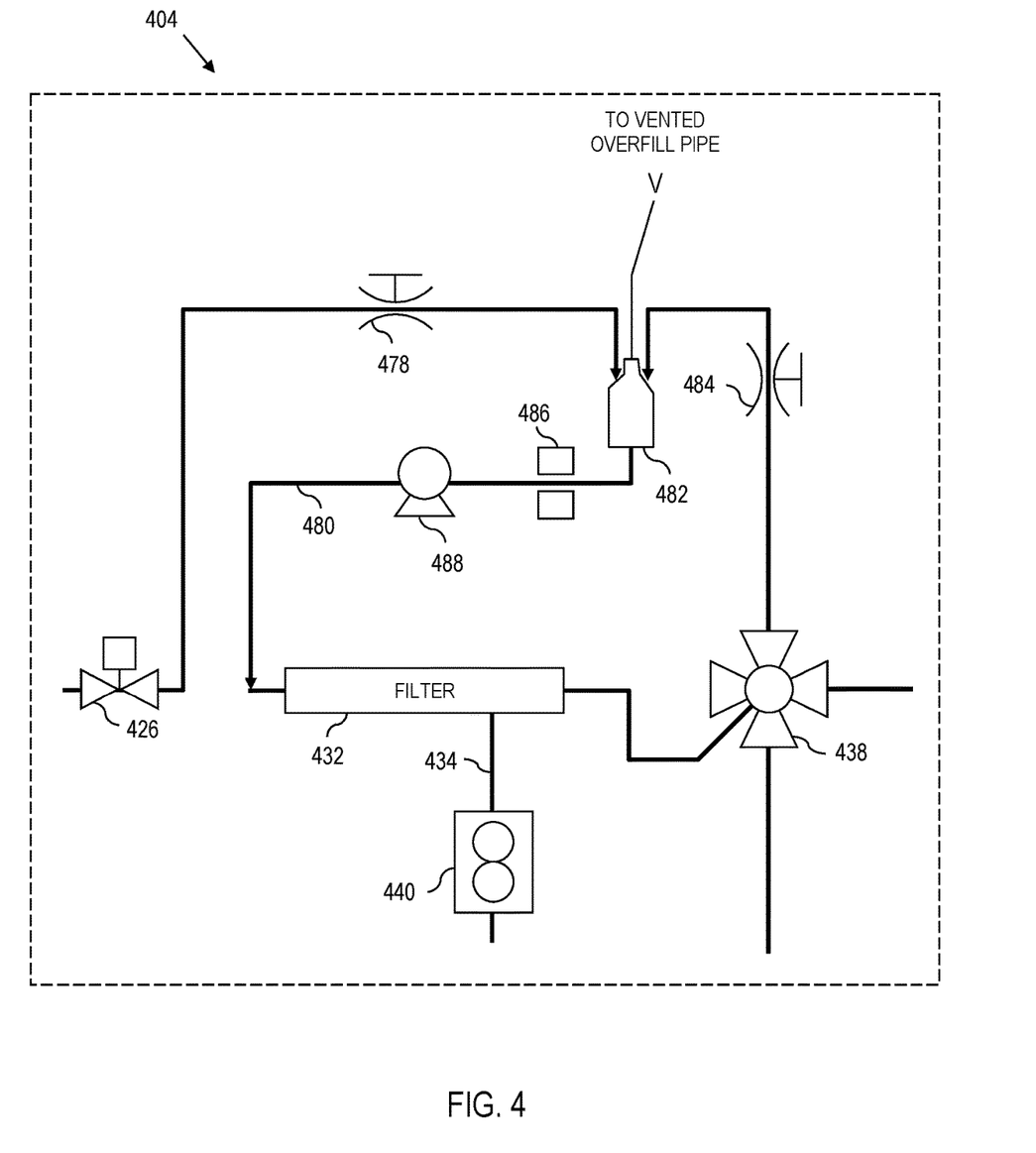
FIG. 4 is a schematic diagram of a liquid concentrator, in accordance with various aspects of the present disclosure.

Referring to FIG. 4, example select components of a concentration stage are illustrated according to aspects of the present disclosure. The illustrated concentration stage 404 is referred to herein as a "Liquid Sample Concentrator" (LSC), and can be utilized for applications analogous to the concentration stage 304 of FIG. 3. In this regard, the LSC can be used in place of the concentration stage 304, with the other components and features disclosed in FIGS. 1-3. As such, like elements are illustrated with corresponding reference numerals.

The concentration stage 404 includes first control valve 426 analogous to the first control valve 326 of FIG. 3. The first control valve 426 is controlled by the controller (see controller 112, FIG. 1; controller 216, FIG. 2; or controller 370, FIG. 3) to open in order to accept a volume of liquid, e.g., on the order of 1 to 100 liters, for processing in an example implementation. In an example embodiment, this "initial volume" is introduced at an elevated pressure that is regulated by the LSC to be in the range, for instance, of 5 to 30 pounds per square inch. This controlled but elevated pressure provides the motive force for the concentration stage 404. The LSC regulates the pressure so that the original source of liquid can have variable characteristics, including a wide range of pressures and being static or flowing. The liquid may also flow through an optional flow restrictor 478 to modify a flow rate of the liquid.

For concentrating microorganisms and other particulates in the liquid, the initial volume is directed into a recirculating loop 480. More particularly, the recirculating loop 480 receives, as an input, liquid through the first control valve 426. Once input, the liquid is processed by a loop that flows from a concentrator reservoir 482 to a tangential flow filter 432 (e.g., analogous to the tangential flow filter 332 of FIG.

3), then to a retentate control valve 438 (analogous to the retentate control valve 338 of FIG. 3), and then back to the concentrator reservoir 482.

As the recirculating liquid passes through the tangential flow filter 432, a fraction of the liquid (but none of the microorganisms) permeates the filter and flows to a permeate path 434. The volume of the liquid that continues circulating is reduced, and the concentration of microorganisms within that volume is increased. The volumetric flow rate of the permeate (e.g., 1 to 3 mL/sec) and the transmembrane pressure of the tangential flow filter 432 (e.g., 3 to 15 psi) are selected to optimize the recovery of microorganisms in the concentrate. Microorganisms may be less likely to be captured by the tangential flow filter surface, or other loop surfaces, under these flow and pressure conditions. The pressure differential across the filter is controlled using a second flow restrictor 484.

The inclusion of the concentrator reservoir 482 (which may be vented to an overfill pipe) as part of the recirculation loop 480 enables the system to process an arbitrarily large volume in stages. In an example implementation, a liquid sensor 486 at an outlet of the concentrator reservoir 482 is used to automatically detect when the volume in the concentrator reservoir 482 is low enough to accept additional liquid. The volume of the liquid processed is measured by the flow meter 440 on the liquid permeate path 434. The controller is programmed with a target process volume and continues refilling the concentrator reservoir 482, and recirculating the concentrated liquid, until that target volume is reached.

Once the controller detects that a defined target is reached, the concentration stage 404 enters a concentrate transfer mode. The goal of the transfer is recovery of all the concentrated liquid. This is achieved by a processes comprising running a recirculation pump 488 in reverse flow, and temporarily placing all the concentrated liquid in the concentrator reservoir 482. The process also comprises rotating the retentate control valve 438 position to close the recirculation loop and open the path to the second reservoir (main reservoir) (e.g., see reservoir 306, FIG. 3). Yet further, the process comprises running the recirculation pump 488 in forward flow, transferring the concentrated liquid from the concentrator reservoir 482 to the reservoir 306 (FIG. 3), and drawing air into the recirculation loop through a filtered vent of the concentrator reservoir 482 to serve as the "makeup air" and allow all liquid to transfer out of the retentate control valve 438 to the main reservoir (e.g., reservoir 306, FIG. 3).

Notably, the main reservoir (e.g., see 306, FIG. 3) receives and holds the concentrated liquid for subsequent transfer to an analysis stage (e.g., analyzer 108, FIG. 1). Because the main reservoir is separated from the recirculation loop 480 by the retentate control valve 438, concentration, transfer, and any subsequent analyses can run in parallel. This parallel processing reduces the effective time per sample. In certain embodiments, the concentration stage 404 is controlled by a controller running the software needed to automate its operation. The controller can interface with another system, such as an analyzer, to operate synchronously, e.g., as described with reference to FIG. 3. Synchronization allows for analysis to also run in parallel with sample preparation, further reducing time to result.

The flow meter 440 quantifies the volume of processed liquid. This information is stored by the control software and is available for subsequent analyses where the material found may need to be quantified relative to the initial volume, e.g., by calculating a cellular concentration.

All components in the concentrator stage 404 are selected to be capable of sterilization and are preferably resistant to microbial contamination to reduce the risk that the concentrated sample is contaminated by microbial material contained inside the concentrator stage 404. For analysis applications, contamination can lead to false positives and inaccurate quantification of cellular material.

In certain embodiments, components in the concentrator stage 404 and the connectors between them, are selected to exclude "dead" volume, regions that fluid can get into and be difficult to get out. Dead volumes encourage bacterial growth, can lead to sample carry over, and can act as reservoirs of unintended chemicals (such as cleaning agents). Certain embodiments here address this issue with a connection of two permeate ports on the filter 432. For such a two-port embodiment, in this configuration, some embodiments only connect one of the ports. However, this creates a dead volume at the second port that can cause any of the problems described above and, thus, an alternative approach is to connect both permeate ports.

Aspects herein address a potential issue of liquid overflow or overpressure. The flow restrictor 478 is included to constrain the rate of fluid transfer into the reservoir 482. In the event of a system power loss, which would stop recirculation but allow for the reservoir 482 to continue to fill, this restricted rate is low enough to not exceed the waste line capacity.

The components that form the recirculating loop are arranged in a manner that minimizes the internal volume of that loop. During concentration, the minimum volume of the liquid (and therefore the maximum concentration of the particles) is determined by the volume of the recirculation loop. Therefore, both the selection of components and the arrangement of those components is used to minimize this volume.

While discussed generally in the context of concentrating microorganisms from the liquid, other particulates can be concentrated with the concentration stage 404. For instance, the filter 432 can be selected to determine what size range of particles are retained and which are excluded. Other non-soluble particles, including proteins and polymers, can be automatically extracted.

Figure 5:
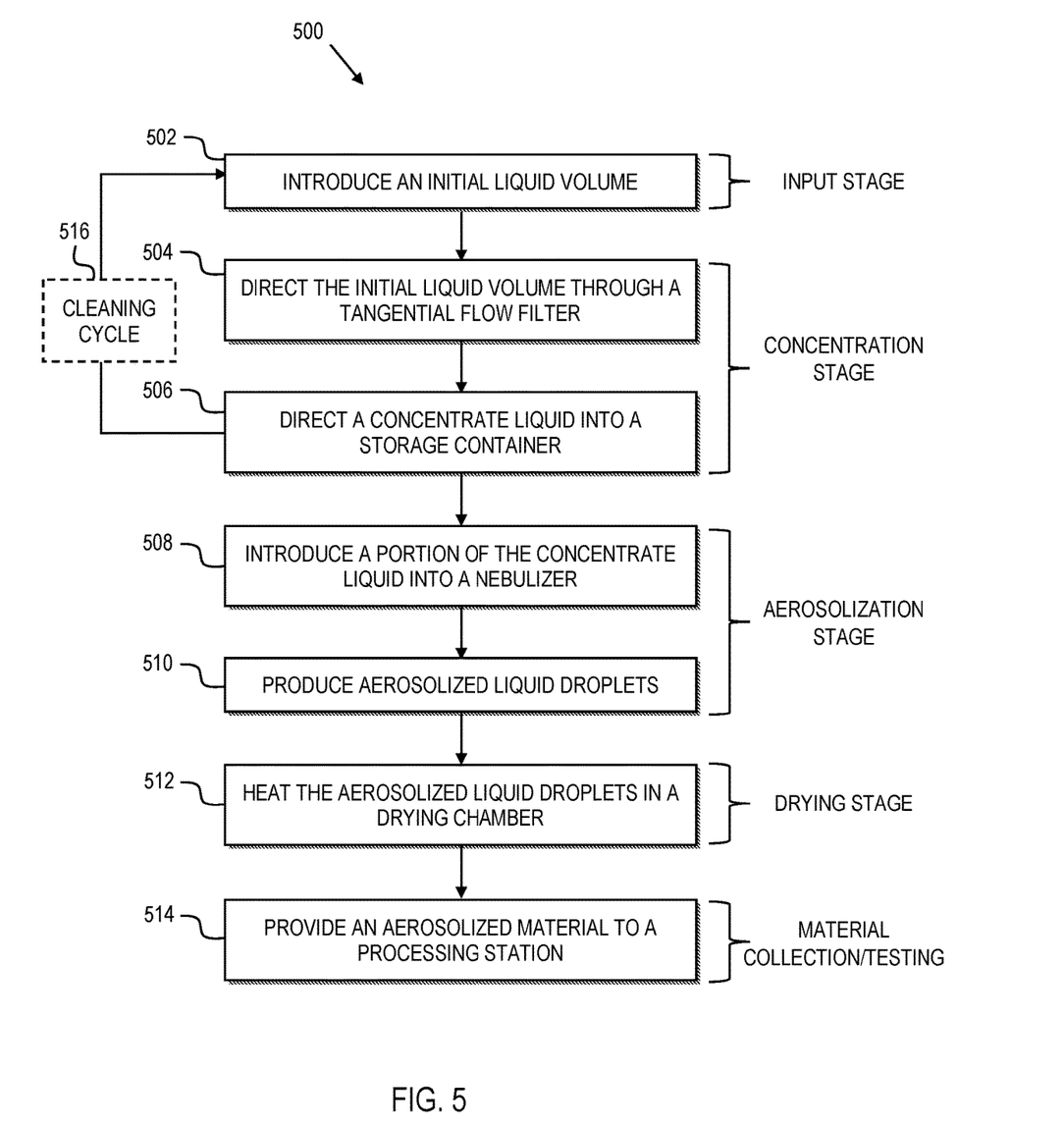
FIG. 5 is a flowchart illustrating a process for extracting a material from a liquid sample, in accordance with various aspects of the present disclosure.

With reference to FIG. 5, a process 500 for extracting a material from a liquid sample is illustrated. The process 500 may be implemented using, for example, any system, apparatus, components, combination of components, combinations of features and capabilities, etc., described with reference to the FIGURES herein.

An input phase of the process 500 includes introducing at 502, an initial liquid volume from a liquid source into a concentration stage for extracting a material from a liquid, examples of which are described more fully herein.

The process 500 also comprises directing, at 504, the initial liquid volume through a tangential flow filter. As set out in greater detail herein, the corresponding apparatus may comprise a plurality of valves that cooperate to define multiple paths for the flow of liquid through the system. The initial liquid volume follows a first path, e.g., a permeate path, from the tangential flow filter and toward a drain line. The liquid may be introduced into the apparatus at an elevated pressure relative to the liquid source. After the initial liquid volume has passed through the tangential flow filter, the tangential flow filter comprises a concentrated liquid with a smaller liquid volume and a higher concentration of the material as compared to the initial liquid volume.

Here, the process optionally comprises directing, at 506, a concentrated liquid into a storage container. For instance, in an example implementation, the concentrated liquid is collected and stored by directing the concentrated liquid along a second path, e.g., a retentate path, and into storage container, e.g., a concentrated liquid reservoir, as described herein. Following collection of the concentrated liquid in the concentration liquid reservoir, a new concentration phase may begin with the introduction of a second initial liquid volume at 502.

The aerosolizing phase of the process 500 begins with introducing, at 508, e.g., by a peristaltic pump, a portion of the concentrated liquid from the concentrated liquid reservoir into an aerosolizing stage, e.g., which includes a nebulizer. The aerosolizing phase also includes producing, at 510, aerosolized liquid droplets. For instance, in the nebulizer, the concentrated liquid is vaporized and turned into aerosolized liquid droplets comprising the material.

The process 500 also comprises a drying stage, which includes heating, at 512, the aerosolized liquid droplets in a drying chamber to separate the material from the liquid. The liquid in the aerosolized liquid droplets evaporates, leaving the aerosolized material in the air within the drying chamber. The peristaltic pump may control the flow of the concentrated liquid at a flow rate that substantially matches a drying capacity of the drying chamber.

The process 500 can then optionally comprise providing, at 514, an aerosolized material to a processing station(s) for storage and/or analysis, examples of which are set out in greater detail herein, e.g., with reference to the analyzer 108 (FIG. 1); analyzer 360 (FIG. 3), etc.

Prior to beginning a new concentration phase, the process 500 may comprise initiating an optional cleaning cycle, 516, in which a cleaning liquid is directed along a third path, e.g., a drain path, to flush out and clean the components of the system associated with the concentration phase.

In some implementations, one or more portions of the process 500 may be fully or partially automated. For example, as described in greater detail herein, a controller may control the introduction and flow of liquid through the system and the handling of the aerosolized material produced by the process 500.

Figure 6:
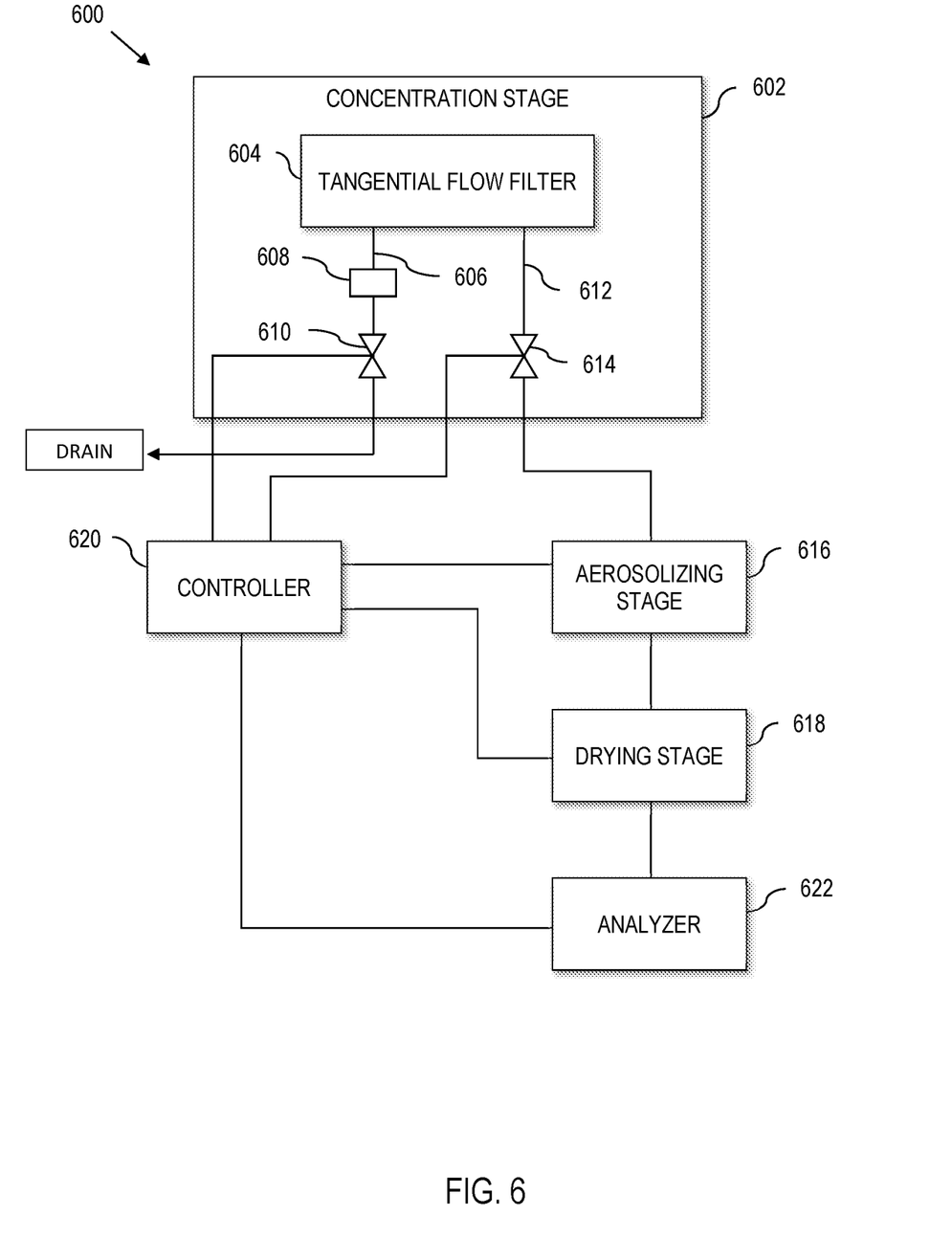
FIG. 6 is a block diagram of another example apparatus for extracting materials from liquids, according to aspects herein.

Referring briefly to FIG. 6, an apparatus 600 for extracting materials from liquids is illustrated according to further aspects of the present disclosure. Analogous to other embodiments described herein, the apparatus 600 includes a concentration stage 602 that accepts an initial liquid volume having an initial concentration of a material. The illustrated concentration stage 602 comprises a tangential flow filter 604 that accepts the initial liquid volume. Also, the tangential flow filter collects the material from the initial liquid volume, produces a permeate that is substantially devoid of the collected material, and produces a retentate having a higher concentration of the material than the initial concentration. The concentration stage 602 also includes a permeate path 606 from the tangential flow filter 604, which defines a conduit for the permeate. In this example embodiment, the permeate path 606 includes a flow meter 608 and a permeate control valve 610 there-along. The concentration stage 602 further includes a retentate path from the tangential flow filter, which defines a conduit for the retentate, the retentate path 612 comprising a retentate control valve 614. An aerosolizing stage 616 is coupled to the retentate path 612. As described more fully herein, the aerosolizing stage 616 converts the retentate into an aerosol. A drying stage 618 dries the aerosol to extract the material onto a material substrate. A controller 620 is coupled to the concentration stage (e.g., to the permeate control valve 610 and to the retentate control valve 614 to sequence the flow of operation in a manner analogous to that described more fully herein. The controller 620 is also coupled to the aerosolizing stage 616, wherein the controller 620 automates liquid sample collection. An analyzer 622 is also coupled to the controller 620, which operates in parallel with the liquid sample collection to monitor, detect, analyze, etc., the previously collected sample.

In this regard, the controller 620 can be coupled to the various components by coupling to meters, sensors, controllable valves, etc., as described more fully herein. Likewise, the analyzer 622 can implement any combination of monitoring, analyzing, and outputting functions, as described more fully herein.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure.

Having thus described the disclosure of the present application in detail and by reference to embodiments thereof, it will be apparent that modifications and variations are possible without departing from the scope of the disclosure defined in the appended claims.

What is claimed is:

1. An apparatus that extracts materials from liquids, the apparatus comprising:
    a concentration stage that accepts an initial liquid volume, the initial liquid volume having an initial concentration of a material, the concentration stage comprising:
        a tangential flow filter that accepts the initial liquid volume, collects the material from the initial liquid volume, produces a permeate that is substantially devoid of the collected material, and produces a retentate that has a higher concentration of the material than the initial concentration;
        a first path from the tangential flow filter that defines a conduit for the permeate; and
        a second path from the tangential flow filter that defines a conduit for the retentate;
    an aerosolizing stage coupled to the second path, wherein the aerosolizing stage converts the retentate into an aerosol; and
    a drying stage that dries the aerosol to extract the material, the extracted material collected onto a material substrate.

2. The apparatus of claim 1, wherein:
    the second path comprises a retentate control valve; and
    the first path comprises:
        a flow meter; and
        a permeate control valve, wherein the permeate control valve is open and the retentate control valve is closed during collection of the material.

3. The apparatus of claim 2, wherein the retentate control valve comprises:
a closed position;
an open position; and
an open to drain position, wherein the open to drain position provides a drain path to prime and clean the tangential flow filter that directs fluid to a drain line and bypasses the aerosolizing stage.

4. The apparatus of claim 3, wherein the drain path directs the liquid through the concentration stage and into the drain line and does not enter the aerosolizing stage.

5. The apparatus of claim 1 further comprising:
a concentrated liquid reservoir located downstream of the tangential flow filter; and
a pressure regulator that controls a pressure of the liquid in the concentration stage, the liquid in the concentration stage operated at a higher pressure than a pressure of a liquid source.

6. The apparatus of claim 1, wherein:
the aerosolizing stage comprises:
a peristaltic pump; and
a nebulizer; and
the drying stage comprises:
a drying chamber,
wherein:
the peristaltic pump controls a flow of the liquid into the nebulizer;
the nebulizer receives the liquid and coverts the received liquid into aerosolized liquid droplets; and
the drying chamber receives the aerosolized liquid droplets and separates cellular material from the droplets.

7. The apparatus of claim 6, wherein the peristaltic pump controls the flow of the liquid into the nebulizer at a flow rate, the flow rate substantially proportional to a drying capacity of the drying chamber.

8. The apparatus of claim 1, further comprising a controller coupled to the concentration stage, the controller further coupled to the aerosolizing stage, wherein the controller automates liquid sample collection.

9. The apparatus of claim 8, wherein the controller is further coupled to an analyzer station, such that liquid sample collection operates in parallel with the analyzer.

10. The apparatus of claim 1, wherein the concentration stage comprises a recirculating loop, the recirculation loop comprising:
a concentrator reservoir that flows to the tangential flow filter; and
a retentate control valve that controls flow back to the concentrator reservoir.

11. A process for extracting materials from liquids, the process comprising:
introducing an initial liquid volume into a concentration stage, the initial liquid volume having an initial concentration of a material;
directing the initial liquid volume into a tangential flow filter, the tangential flow filter for entrapping the material to produce a concentrated liquid, the concentrated liquid having a higher concentration of the material than the initial concentration; and
directing the concentrated liquid out of the concentration stage;
introducing a portion of the concentrated liquid into an aerosolizing stage comprising a nebulizer to produce aerosolized liquid droplets; and
heating the aerosolized liquid droplets in a drying stage comprising a drying chamber to extract the material from the liquid droplets.

12. The method of claim 11 further comprising providing the extracted material to an analyzer to classify particulates contained within the extracted material.

13. The method of claim 11 further comprising:
directing the concentrated liquid into a storage container; and
introducing a second liquid volume upon directing the concentrated liquid into the storage container.

14. The method of claim 11 further comprising controlling a pressure of the initial liquid volume upon introducing the initial liquid volume into the concentration stage, the pressure of the initial liquid volume being higher than a pressure of a liquid source.

15. The method of claim 11 further comprising controlling a flow rate of the concentrated liquid into the nebulizer, the flow rate being substantially proportional to a drying capacity of the drying chamber.

16. The method of claim 11, wherein directing the initial liquid volume into the tangential flow filter comprises directing the initial liquid volume along a permeate path such that a portion of the initial liquid volume flows through the tangential flow filter and toward a drain line.

17. The method of claim 11, wherein directing a concentrated liquid out of the concentration stage comprises directing the concentrated liquid along a retentate path into a storage container.

18. The method of claim 17 further comprising initiating a cleaning cycle, the cleaning cycle being initiated after directing the concentrated liquid along the retentate path into the storage container, the cleaning cycle further being initiated prior to introducing a second liquid volume into the concentration stage.

19. The method of claim 18, wherein the cleaning cycle comprises directing a cleaning liquid along a drain path when:
a selector valve is in an open position;
a first control valve is in an open position; and
a second control valve is in a closed position.

20. An apparatus for extracting materials from liquids, the apparatus comprising:
a concentration stage that accepts an initial liquid volume, the initial liquid volume having an initial concentration of a material, the concentration stage comprising:
a tangential flow filter that accepts the initial liquid volume, the tangential flow filter further collects the material from the initial liquid volume, the tangential flow filter further produces a permeate that is substantially devoid of the collected material, the tangential flow filter further produces a retentate, the retentate having a higher concentration of the material than the initial concentration;
a permeate path from the tangential flow filter, which defines a conduit for the permeate, the permeate path comprising:
a flow meter; and
a permeate control valve; and
a retentate path from the tangential flow filter, which defines a conduit for the retentate, the retentate path comprising a retentate control valve;
an aerosolizing stage coupled to the retentate path, wherein the aerosolizing stage converts the retentate into an aerosol;

a drying stage that dries the aerosol to extract the material, wherein the extracted material is collected onto a material substrate;

a controller coupled to the concentration stage, the controller further coupled to the aerosolizing stage, wherein the controller automates liquid sample collection; and an analyzer coupled to the controller, which operates in parallel with the liquid sample collection.

* * * * *